United States Patent
Allen, IV

(10) Patent No.: US 10,206,736 B2
(45) Date of Patent: Feb. 19, 2019

(54) SURGICAL FORCEPS WITH SCALPEL FUNCTIONALITY

(71) Applicant: COVIDIEN LP, Mansfield, MA (US)

(72) Inventor: James D. Allen, IV, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 652 days.

(21) Appl. No.: 14/657,553

(22) Filed: Mar. 13, 2015

(65) Prior Publication Data
US 2016/0262826 A1 Sep. 15, 2016

(51) Int. Cl.
*A61B 18/14* (2006.01)
*A61B 17/295* (2006.01)
(Continued)

(52) U.S. Cl.
CPC ........ *A61B 18/1445* (2013.01); *A61B 17/295* (2013.01); *A61B 17/2909* (2013.01); *A61B 34/37* (2016.02); *A61B 17/3211* (2013.01); *A61B 2017/00353* (2013.01); *A61B 2017/2902* (2013.01); *A61B 2017/2925* (2013.01); *A61B 2017/2946* (2013.01);
(Continued)

(58) Field of Classification Search
CPC .............. A61B 17/285; A61B 17/2833; A61B 2017/2946; A61B 2017/2902; A61B 2018/1455
See application file for complete search history.

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

Extended European search report issued in corresponding EP application No. 161597589.3 dated Aug. 26, 2016.
(Continued)

*Primary Examiner* — Jaymi Della
*Assistant Examiner* — Sean W Collins

(57) ABSTRACT

A surgical forceps includes a knife bar having a knife translatable between a retracted position, a first extended position, and a second extended position. A trigger is operably coupled with the knife bar such that movement of the trigger between an un-actuated position, a first actuated position, and a second actuated position correspondingly moves the knife. An actuator is movable between locked and unlocked positions such that: with the trigger in the un-actuated or first actuated position and the actuator in the locked position, movement of the trigger to the second actuated position is inhibited; with the trigger in the second actuated position and the actuator in the locked position, the trigger is retained in the second actuated position; and with the actuator in the unlocked position, the trigger is movable between the un-actuated or first actuated position and the second actuated position.

7 Claims, 6 Drawing Sheets

(51) Int. Cl.
*A61B 17/29* (2006.01)
*A61B 34/37* (2016.01)
A61B 18/00 (2006.01)
A61B 17/00 (2006.01)
A61B 17/3211 (2006.01)

(52) U.S. Cl.
CPC .............. *A61B 2018/00595* (2013.01); *A61B 2018/00607* (2013.01); *A61B 2018/145* (2013.01); *A61B 2018/1455* (2013.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| 5,312,391 A | 5/1994 | Wilk |
| 5,318,040 A | 6/1994 | Kensey et al. |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,445,638 A | 8/1995 | Rydell et al. |
| D384,413 S | 9/1997 | Zlock et al. |
| H1745 H | 4/1998 | Paraschac |
| D402,028 S | 12/1998 | Grimm et al. |
| D408,018 S | 4/1999 | McNaughton |
| 5,893,863 A | 4/1999 | Yoon |
| 5,919,202 A | 7/1999 | Yoon |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| 6,190,386 B1 | 2/2001 | Rydell |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,616,661 B2 | 9/2003 | Wellman et al. |
| 6,679,882 B1 | 1/2004 | Kornerup |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 7,063,699 B2 | 6/2006 | Hess et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| 7,232,440 B2 | 6/2007 | Dumbauld et al. |
| D547,154 S | 7/2007 | Lee |
| D564,662 S | 3/2008 | Moses et al. |
| D567,943 S | 4/2008 | Moses et al. |
| 7,367,976 B2 | 5/2008 | Lawes et al. |
| D575,395 S | 8/2008 | Hushka |
| D575,401 S | 8/2008 | Hixson et al. |
| 7,445,621 B2 | 11/2008 | Dumbauld et al. |
| D582,038 S | 12/2008 | Swoyer et al. |
| 7,481,810 B2 | 1/2009 | Dumbauld et al. |
| 7,510,562 B2 | 3/2009 | Lindsay |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 2004/0236326 A1 | 11/2004 | Schulze et al. |
| 2008/0027448 A1* | 1/2008 | Raus ................ A61B 17/1611 606/79 |
| 2009/0112206 A1* | 4/2009 | Dumbauld ......... A61B 18/1445 606/51 |
| 2009/0125027 A1 | 5/2009 | Fischer |
| 2010/0185196 A1 | 7/2010 | Sakao et al. |
| 2011/0130757 A1 | 6/2011 | Horlle et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 2591744 A1 | 5/2013 |
| EP | 2628459 A2 | 8/2013 |
| EP | 2653120 A2 | 10/2013 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |

(56) References Cited

FOREIGN PATENT DOCUMENTS

| | | |
|---|---|---|
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999. (1 page).
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

(56) References Cited

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.
U.S. Appl. No. 14/065,644, filed Oct. 29, 2013; inventor: Reschke.

\* cited by examiner

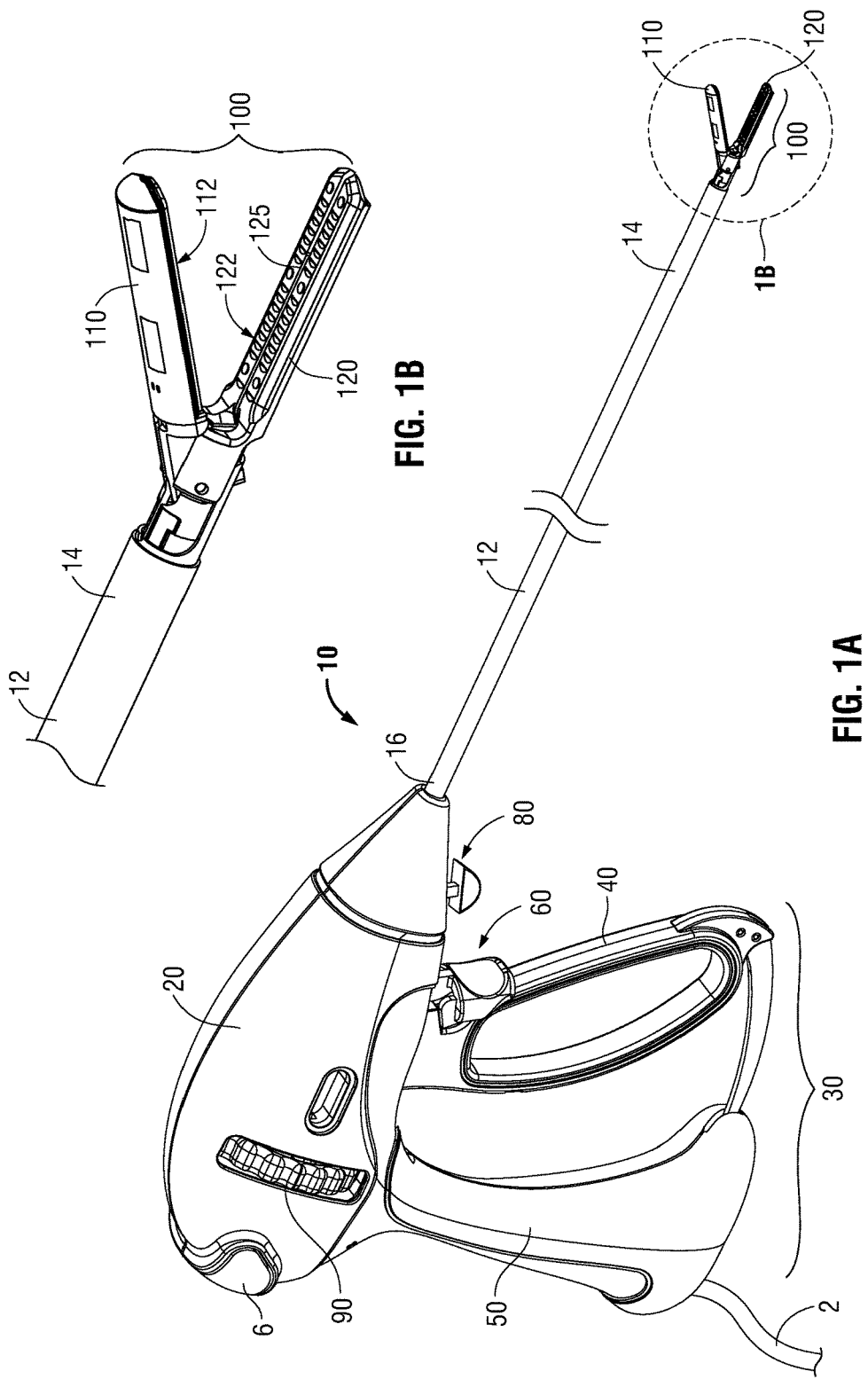

SURGICAL FORCEPS WITH SCALPEL FUNCTIONALITY

BACKGROUND

Technical Field

The present disclosure relates to surgical instruments and, more particularly, to surgical forceps for grasping and/or treating tissue that incorporates a retractable knife capable of being used as a scalpel.

Background of Related Art

A forceps is a plier-like instrument which relies on mechanical action between its jaws to grasp, clamp and constrict tissue. Electrosurgical forceps utilize both mechanical clamping action and electrical energy to affect hemostasis by heating tissue to treat, e.g., coagulate, cauterize, and/or seal, tissue. Typically, once tissue is treated, the surgeon has to accurately sever the treated tissue. Accordingly, electrosurgical forceps have been designed which incorporate a knife or blade member which effectively severs the tissue after electrosurgical treatment thereof.

In some surgical procedures, it is necessary to dissect through one or more layers of tissue, for example, in order to reach underlying tissue(s) to be treated and/or divided. As can be appreciated, it may be beneficial, particularly with respect to endoscopic surgical procedures, to provide a single instrument capable of performing both of these tasks, thereby obviating the need to alternatingly remove and insert different instruments in favor of one another.

SUMMARY

As used herein, the term "distal" refers to the portion of the instrument or component thereof that is being described which is further from a user, while the term "proximal" refers to the portion of the instrument or component thereof that is being described which is closer to a user. Further, to the extent consistent, any of the aspects disclosed herein may be used in conjunction with any or all of the other aspects disclosed herein.

In accordance with aspects of the present disclosure, a surgical forceps is provided including a housing, a shaft extending distally from the housing, an end effector assembly disposed at a distal end of the shaft and including first and second jaw members configured for grasping tissue therebetween, a knife assembly, a trigger assembly, and a knife lock assembly. The knife assembly is disposed within the shaft and includes a knife bar having a knife disposed at a distal end thereof. The knife bar is longitudinally translatable through the shaft and relative to the end effector assembly to translate the knife between a retracted position, wherein the knife is disposed proximally of the end effector assembly, a first extended position, wherein the knife extends between the first and second jaw members, and a second extended position, wherein the knife extends distally from the first and second jaw members. The trigger assembly is associated with the housing and includes a trigger operably coupled with the knife bar such that movement of the trigger between an un-actuated position, a first actuated position, and a second actuated position moves the knife between the retracted position, the first extended position, and the second extended position, respectively. The knife lock assembly is associated with the housing and includes an actuator movable between a locked position and an unlocked position. With the trigger disposed in the un-actuated position or the first actuated position and the actuator disposed in the locked position, movement of the trigger to the second actuated position is inhibited. With the trigger disposed in the second actuated position and the actuator disposed in the locked position, the trigger is retained in the second actuated position. With actuator disposed in the unlocked position, the trigger is movable between the un-actuated position or the first actuated position and the second actuated position.

In an aspect of the present disclosure, the trigger assembly includes a slider coupled between the trigger and the knife bar. In such aspects, with the trigger disposed in the un-actuated position or the first actuated position and the actuator disposed in the locked position, the actuator interferes with the slider to inhibit movement of the trigger to the second actuated position; with the trigger disposed in the second actuated position and the actuator disposed in the locked position, the actuator engages the slider to inhibit movement of the slider, thereby retaining the trigger in the second actuated position; and with actuator disposed in the unlocked position, the actuator permits translation of the slider therethrough such that the trigger is movable between the un-actuated position or the first actuated position and the second actuated position.

In another aspect of the present disclosure, the slider includes a proximal mandrel operably coupling the trigger with the knife bar and a distal mandrel operably associated with the actuator.

In yet another aspect of the present disclosure, the actuator is biased towards the locked position.

In still another aspect of the present disclosure, the actuator includes an actuator button disposed on the housing. The actuator button is selectively depressible relative to the housing to move the actuator from the locked position to the unlocked position.

In still yet another aspect of the present disclosure, the forceps further includes a drive assembly including a drive bar slidably disposed within the shaft. The drive bar is coupled to at least one of the first and second jaw members at a distal end thereof. The forceps, in such aspects, further includes a handle assembly associated with the housing and including a movable handle operably coupled with the drive bar. The movable handle is movable between an initial position and a compressed position for moving the first and second jaw members from a spaced-apart position to an approximated position for grasping tissue therebetween.

In another aspect of the present disclosure, each of the first and second jaw members includes an electrically-conductive surface adapted to connect to a source of energy for treating tissue grasped between the first and second jaw members.

In still another aspect of the present disclosure, each of the first and second jaw members defines a knife slot configured to permit reciprocation of the knife therethrough.

Another surgical forceps provided in accordance with aspects of the present disclosure includes a housing, a shaft extending distally from the housing, an end effector assembly disposed at a distal end of the shaft and including first and second jaw members configured for grasping tissue therebetween, a knife assembly, a slider, a trigger assembly, and a knife lock assembly. The knife assembly is disposed within the shaft and includes a knife bar having a knife disposed at a distal end thereof. The knife bar is longitudinally translatable through the shaft and relative to the end effector assembly to translate the knife between a retracted position, wherein the knife is disposed proximally of the end effector assembly, a first extended position, wherein the knife extends between the first and second jaw members, and a second extended position, wherein the knife extends distally from the first and second jaw members. The slider is operably coupled to the knife bar. The trigger assembly is associated with the housing and includes a trigger operably coupled with the slider such that movement of the trigger between an un-actuated position, a first actuated position, and a second actuated position moves the knife between the retracted position, the first extended position, and the second extended position, respectively. The knife lock assembly is associated with the housing and includes an actuator movable between a locked position and an unlocked position. In the locked position, the actuator interferes with the slider to inhibit movement of the trigger from the un-actuated position or the first actuated position to the second actuated position. In the unlocked position, the actuator permits movement of the trigger between the un-actuated position or the first actuated position and the second actuated position.

In an aspect of the present disclosure, the slider includes a proximal mandrel operably coupling the trigger with the knife bar and a distal mandrel operably associated with the actuator.

In another aspect of the present disclosure, the actuator is biased towards the locked position.

In still another aspect of the present disclosure, the actuator includes an actuator button disposed on the housing. The actuator button is selectively depressible relative to the housing to move the actuator from the locked position to the unlocked position.

In yet another aspect of the present disclosure, a drive assembly including a drive bar slidably disposed within the shaft is provided with the surgical forceps. The drive bar is coupled to at least one of the first and second jaw members at a distal end thereof. In such aspects, a handle assembly associated with the housing and including a movable handle operably coupled with the drive bar is also provided. The movable handle is movable between an initial position and a compressed position for moving the first and second jaw members from a spaced-apart position to an approximated position for grasping tissue therebetween.

In still yet another aspect of the present disclosure, each of the first and second jaw members includes an electrically-conductive surface adapted to connect to a source of energy for treating tissue grasped between the first and second jaw members.

In another aspect of the present disclosure, each of the first and second jaw members defines a knife slot configured to permit reciprocation of the knife therethrough.

BRIEF DESCRIPTION OF THE DRAWINGS

Various aspects of the present disclosure are described herein with reference to the drawings wherein like reference numerals identify similar or identical elements:

FIG. 1A is a side, perspective view of an endoscopic surgical forceps provided in accordance with the present disclosure;

FIG. 1B is an enlarged, side, perspective view of the distal end of the forceps of FIG. 1A;

DETAILED DESCRIPTION

Figure 2A:
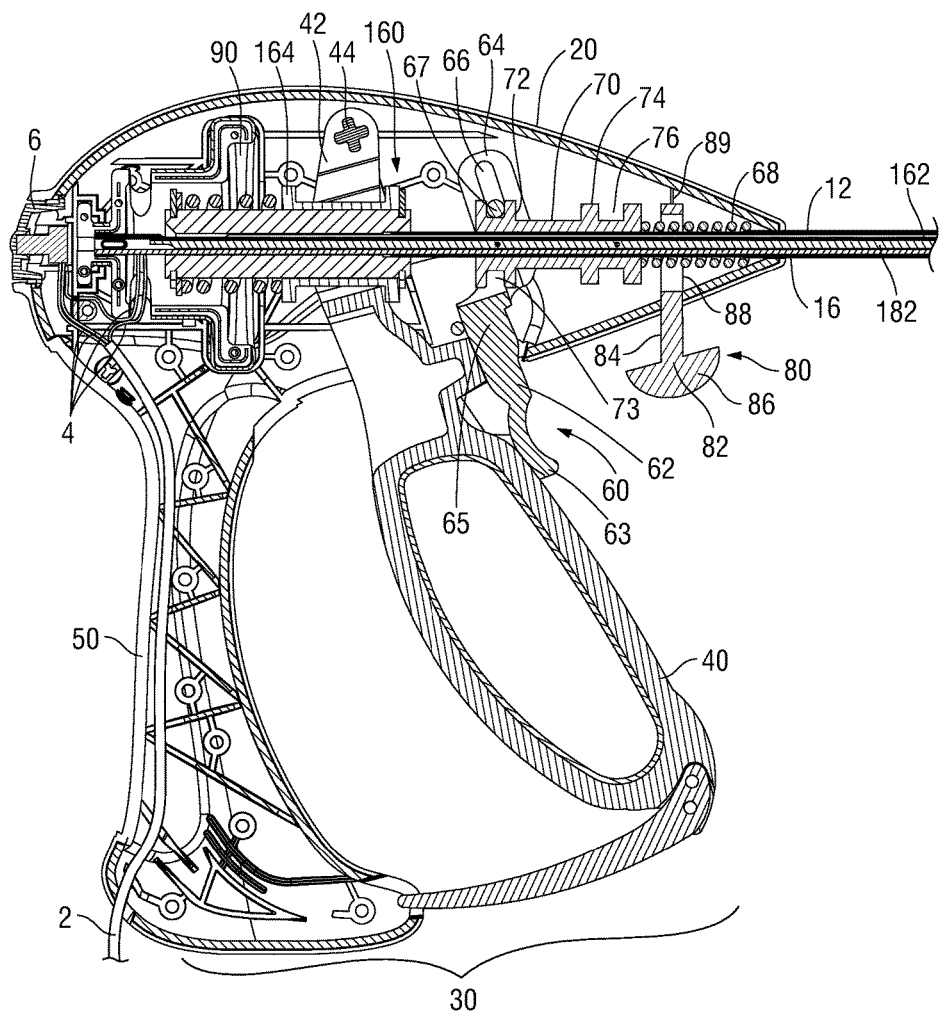
FIG. 2A is a side, cross-sectional view of the proximal end of the forceps of FIG. 1A, wherein the movable handle is disposed in an initial position and the trigger is disposed in an un-actuated position.

Referring to FIGS. 1A and 1B, an electrosurgical forceps 10 for use in connection with endoscopic surgical procedures is shown, although forceps 10 may also be configured for use in connection with traditional open surgical procedures and/or with any suitable form of energy. Forceps 10 generally includes a housing 20, a handle assembly 30, a trigger assembly 60, a knife lock assembly 80, a rotating assembly 90, and an end effector assembly 100. End effector assembly 100 includes first and second jaw members 110, 120, respectively, at least one of which is configured to pivot relative to the other between a spaced-apart position (FIG. 2B) and an approximated position (FIG. 3B) for grasping tissue therebetween. Forceps 10 further includes a shaft 12 having a distal end 14 configured to engage end effector assembly 100 and a proximal end 16 that engages housing 20. Rotating assembly 90 is rotatable in either direction to rotate end effector assembly 100 relative to shaft 12 and housing 20 in either direction. Housing 20 houses the internal working components of forceps 10.

Forceps 10 also includes an electrosurgical cable 2 that connects forceps 10 to a generator (not shown) or other suitable power source, although forceps 10 may alternatively be configured as a battery powered instrument. Cable 2 includes a wire (or wires) 4 extending therethrough, into housing 20 and through shaft 12, to ultimately connect the source of energy to jaw member 110 and/or jaw member 120 of end effector assembly 100. An activation switch 6 mounted on housing 20 is electrically coupled between end effector assembly 100 and cable 2 so as to enable the selective supply of energy to jaw member 110 and/or jaw member 120, e.g., upon activation of activation switch 6. However, other suitable electrical connections and/or configurations for supplying energy to jaw member 110 and/or jaw member 120 may alternatively be provided.

End effector assembly 100 is attached at distal end 14 of shaft 12 and includes a pair of opposing jaw members 110 and 120. End effector assembly 100 is designed as a unilateral assembly, i.e., where jaw member 120 is fixed relative to shaft 12 and jaw member 110 is moveable relative to both shaft 12 and fixed jaw member 120. However, end effector assembly 100 may alternatively be configured as a bilateral assembly, i.e., where both jaw member 110 and jaw member 120 are moveable relative to one another and with respect to shaft 12. Each jaw member 110, 120 includes an electrically-conductive tissue-contacting surface 112, 122 disposed thereon. Surfaces 112, 122 are positioned on jaw members 110, 120, respectively, to oppose one another for grasping and treating tissue disposed between jaw members 110, 120.

Figure 2B:
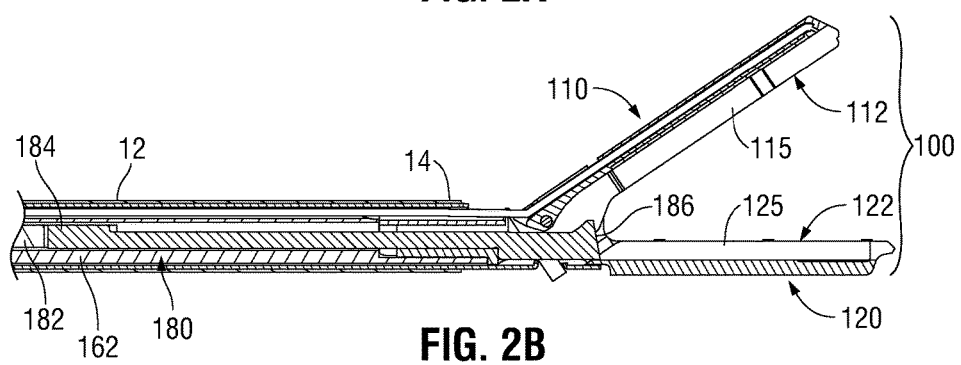
FIG. 2B is a side, cross-sectional view of the distal end of the forceps of FIG. 1A, wherein jaw members of the end effector assembly are disposed in a spaced-apart position corresponding to the initial position of the movable handle and wherein a knife is disposed in a retracted position corresponding to the un-actuated position of the trigger.
Figure 3A:
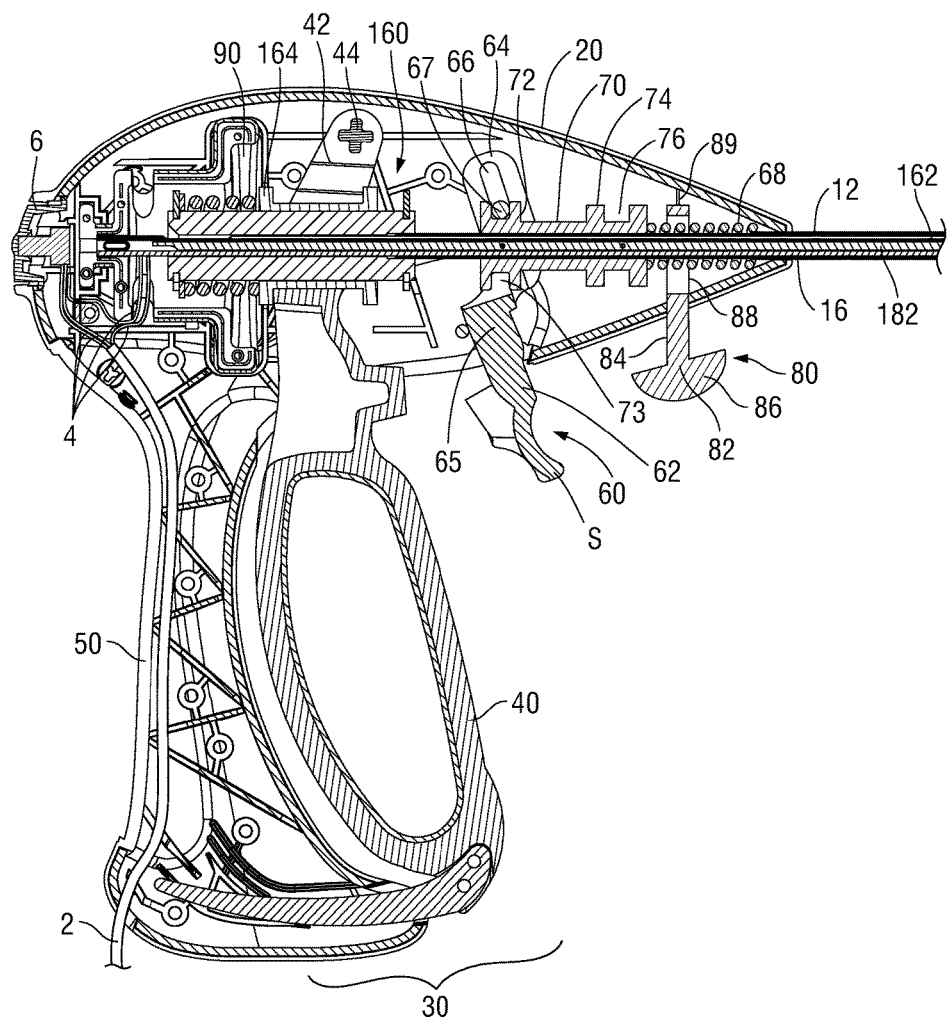
FIG. 3A is a side, cross-sectional view of the proximal end of the forceps of FIG. 1A, wherein the movable handle is disposed in a depressed position and the trigger is disposed in the un-actuated position.
Figure 3B:
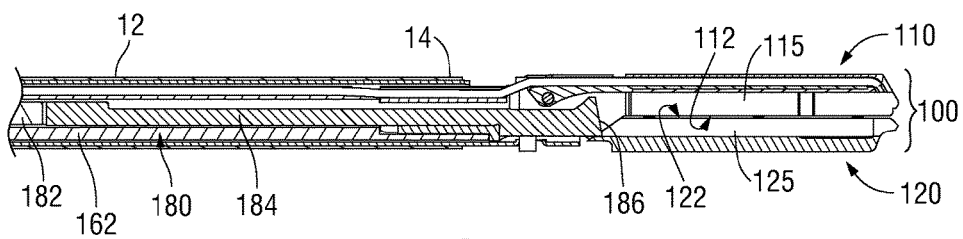
FIG. 3B is a side, cross-sectional view of the distal end of the forceps of FIG. 1A, wherein the jaw members of the end effector assembly are disposed in an approximated position corresponding to the depressed position of the movable handle and wherein the knife is disposed in a retracted position corresponding to the un-actuated position of the trigger.

With additional reference to FIGS. 2A-3B, handle assembly 30 includes a fixed handle 50 and a movable handle 40. Fixed handle 50 is integrally associated with housing 20 and movable handle 40 is movable relative to fixed handle 50. Movable handle 40 is ultimately connected to a drive assembly 160 that, together, mechanically cooperate to impart movement of jaw members 110 and 120 between the spaced-apart and approximated positions to grasp tissue between surfaces 112, 122, respectively. More specifically, movable handle 40 includes a bifurcated flange portion 42 that is pivotably coupled within housing 20 via a pivot 44 and is operably coupled with drive bar 162 of drive assembly 160 via a drive mandrel 164 such that pivoting of movable handle 40 towards fixed handle 30 effects longitudinal translation of drive mandrel 164 and, thus, drive bar 162 through housing 20 and shaft 12. Drive bar 162 is slidably disposed within shaft 12 and is coupled to jaw member 110 at the distal end thereof such that, as drive bar 162 is translated proximally through shaft 12, jaw member 110 is pivoted relative to jaw member 120 from the spaced-apart position (FIG. 2B) towards the approximated position (FIG. 3B). On the other hand, when movable handle 40 is released or returned to its initial position relative to fixed handle 30, drive bar 162 is translated distally, thereby pivoting jaw member 110 relative to jaw member 120 from the approximated position (FIG. 3B) back towards the spaced-apart position (FIG. 2B). However, this configuration may be reversed, e.g., where proximal translation of drive bar 162 moves jaw members 110, 120 towards the spaced-apart position and distal translation of drive bar 162 moves jaw members 110, 120 towards the approximated position.

As shown in FIG. 2A, moveable handle 40 is initially spaced-apart from fixed handle 50 and, correspondingly, jaw members 110, 120 are disposed in the spaced-apart position (FIG. 2B). Moveable handle 40 is depressible from this initial position to a compressed position corresponding to the approximated position of jaw members 110, 120 (see FIGS. 3A and 3B). With tissue grasped between surfaces 112, 122 of jaw members 110, 120, respectively, electrosurgical energy may be conducted between surfaces 112, 122, e.g., upon actuation of activation switch 6, to treat tissue grasped between jaw members 110, 120.

Figure 4A:
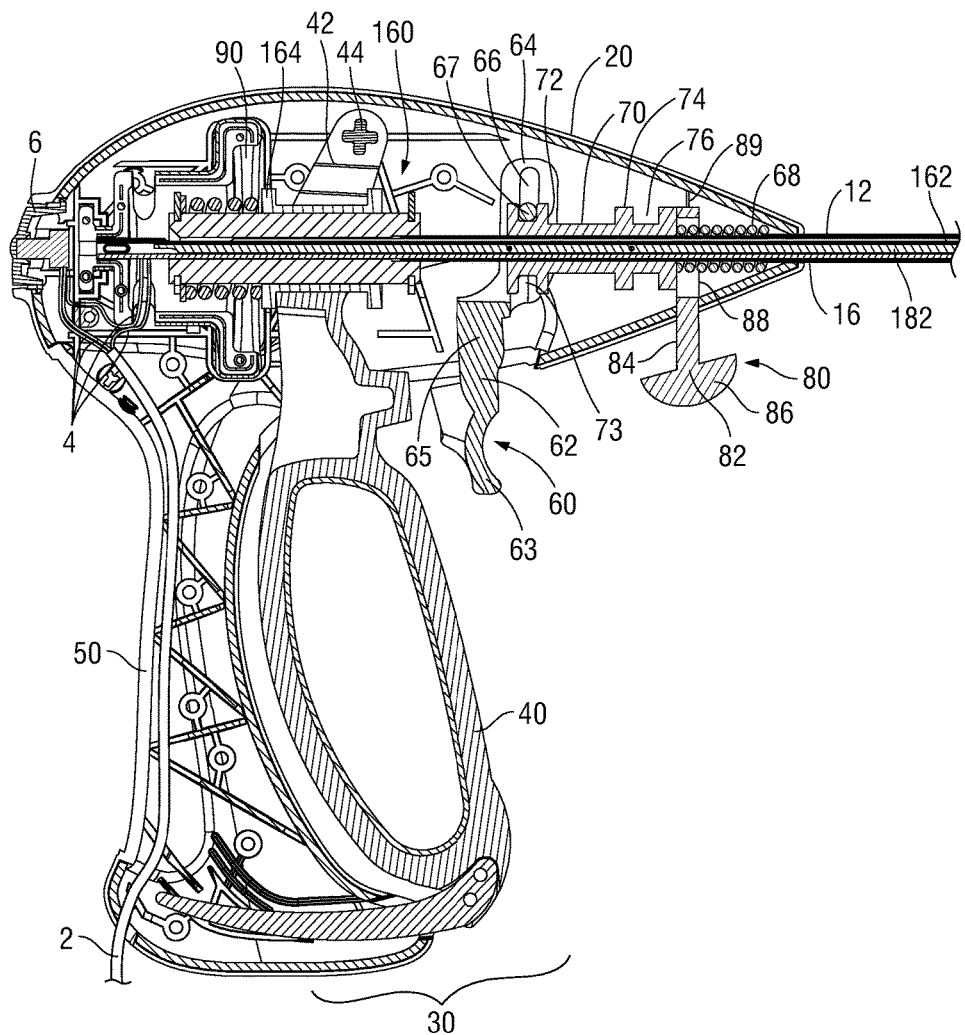
FIG. 4A is a side, cross-sectional view of the proximal end of the forceps of FIG. 1A, wherein the movable handle is disposed in an depressed position and the trigger is disposed in a first actuated position.
Figure 4B:
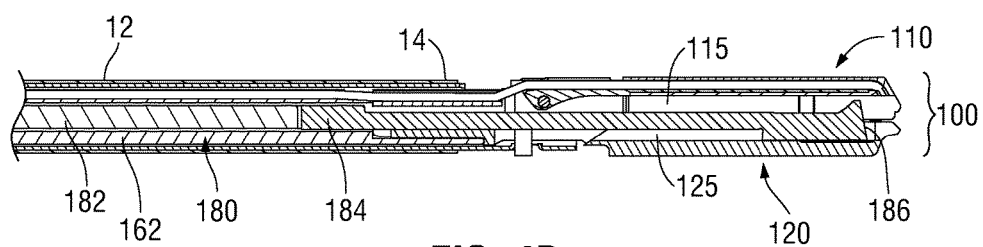
FIG. 4B is a side, cross-sectional view of the distal end of the forceps of FIG. 1A, wherein the jaw members of the end effector assembly are disposed in the approximated position corresponding to the depressed position of the movable handle and the knife is disposed in a first extended position corresponding to the first actuated position of the trigger.
Figure 5A:
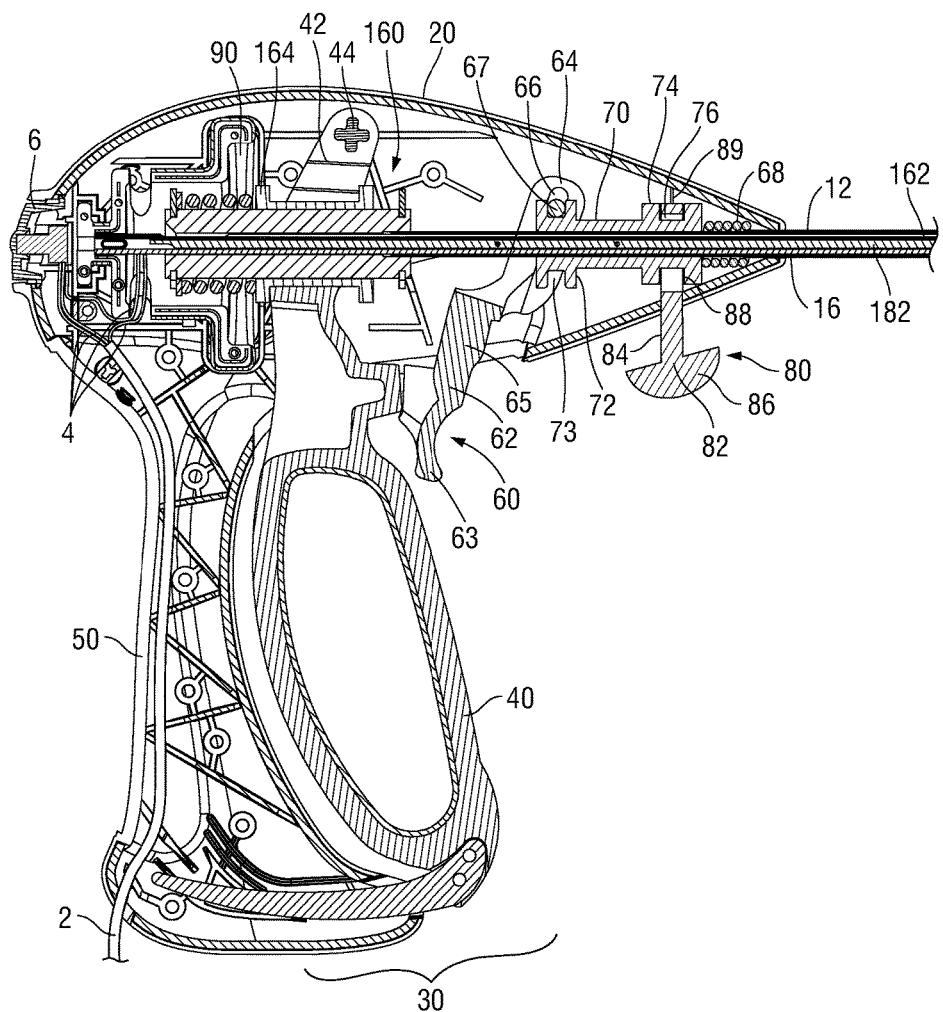
FIG. 5A is a side, cross-sectional view of the proximal end of the forceps of FIG. 1A, wherein the movable handle is disposed in an depressed position, the trigger is disposed in a second actuated position, and a knife lock assembly is disposed in a locked configuration.
Figure 5B:
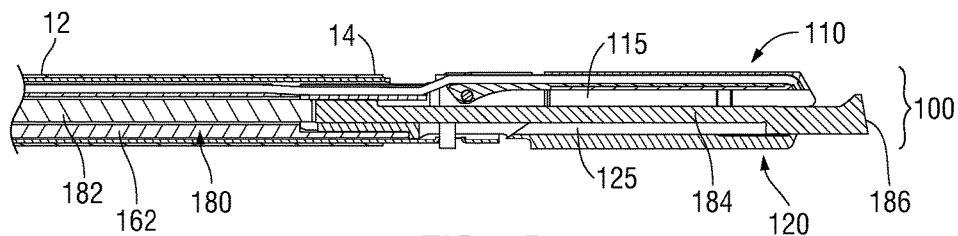
FIG. 5B is a side, cross-sectional view of the distal end of the forceps of FIG. 1A, wherein the jaw members of the end effector assembly are disposed in the approximated position corresponding to the depressed position of the movable handle and the knife is retained in a second extended position corresponding to the second actuated position of the trigger and the locked configuration of the knife lock assembly.

Referring to FIGS. 1A, 1B, and 3A-5B, a knife assembly 180 is disposed within shaft 12 and a knife channel 115, 125 is defined within one or both of jaw members 110, 120, respectively, to permit reciprocation of a knife 184 therethrough for cutting tissue grasped between jaw members 110, 120. Trigger 62 of trigger assembly 60 is operably coupled to knife 184 to advance knife 184 between a retracted position (FIG. 3B), wherein knife 184 is disposed within shaft 12, a first extended position (FIG. 4B), wherein knife 184 extends through knife channels 115, 125 defined within jaw members 110, 120 (but does not extend distally beyond jaw members 110, 120) to cut tissue grasped therebetween, and a second extended position (FIG. 5B), wherein knife 184 extends distally from jaw members 110, 120 to enable use of knife 184 as a scalpel. Knife channels 115, 125 define open distal ends so as to permit extension of knife 184 to the second extended position (FIG. 5B), although other configurations are also contemplated, e.g., knife 184 may be configured to ramp below surface 122 of jaw member 120 and through an aperture defined within the distal end of jaw member 120 to permit extension of knife 184 to the second extended position (FIG. 5B).

Knife assembly 180 further includes a knife bar 182 that is slidably disposed within drive bar 162. Knife 184 is coupled to knife bar 182 at the proximal end of knife 184, while the distal end of knife 184 defines a cutting blade 186 configured to facilitate cutting of tissue. Trigger assembly 60 includes trigger 62 pivotably coupled to housing 20 and movable relative thereto between an un-actuated position (FIG. 3A), a first actuated position (FIG. 4A), and a second actuated position (FIG. 5A) for translating knife 184 between the retracted position (FIG. 3B), the first extended position (FIG. 4B), and the second extended position (FIG. 5B). More specifically, trigger 62 includes a manipulation portion 63 extending from housing 20 to enable actuation of trigger 62 by a user, a bifurcated flange portion 64 (only one leg of the bifurcated flange portion 64 is illustrated in FIGS. 2A, 3A, 4A, and 5A) to enable illustration of the components disposed therebetween) extending upwardly into housing 20, and an intermediate portion 65 disposed between manipulation portion 63 and bifurcated flange portion 64 and about which trigger 62 is pivotably coupled to housing 20. Each leg of bifurcated flange portion 64 defines a slot 66 therethrough. A pin 67 extends through slots 66 and between the legs of bifurcated flange portion 64. Pin 67 is engaged within an annular slot 73 defined within proximal mandrel 72 of slider 70. Slider 70 is slidably disposed about drive bar 162 and engaged with knife bar 182, e.g., via a pin (not shown) engaged with slider 70 and knife bar 182 and extending through a slot (not shown) defined within drive bar 162 such that pivoting of trigger 62 from the un-actuated position (FIG. 3A) to the first actuated position (FIG. 4A) urges bifurcated flange portion 64 distally, thereby urging proximal mandrel 72 and slider 70 distally and, thus, translating knife bar 182 distally through drive bar 162 and shaft 12 and relative to end effector assembly 100 to deploy knife 184. A biasing member 68 may be disposed within housing 20 and positioned to bias slider 70 proximally, thereby biasing knife 184 towards the retracted position (FIG. 3B) and trigger 62 towards the un-actuated position (FIG. 3A).

Continuing with reference to FIGS. 1A, 1B, and 3A-5B, knife lock assembly 80 includes a lock/unlock actuator 82 including a base 84 slidably disposed within housing 20 in generally vertical orientation (generally perpendicular to the longitudinally-extending shaft 12, drive bar 162, and knife bar 182) and an actuator button 86 disposed at an end of base 84 to facilitate actuation of lock/unlock actuator 82. As detailed below, lock/unlock actuator 82 is selectively actuatable to permit movement of trigger 62 from the un-actuated position (FIG. 3A) or the first actuated position (FIG. 4A) to the second actuated position (FIG. 5A), thus permitting extension of knife 184 from the retracted position (FIG. 3B) or the first extended position (FIG. 4B) to the second extended position (FIG. 5A).

Base 84 of lock/unlock actuator 82 of knife lock assembly 80 defines a vertical slot 88 therein so as to permit passage of drive bar 162 (and knife bar 182, which is disposed within drive bar 162) therethrough. Initially, in a locked position of actuator 82, vertical slot 88 is off-center relative to drive bar 162 such that at least a portion of base 84 inhibits the translation of slider 70 so as to inhibit actuation of trigger 62 beyond the first actuated position (FIG. 4A), thereby inhibiting extension of knife 184 beyond the first extended position (FIG. 4B). More specifically, base 84 interferes with distal mandrel 74 of slider 70 to inhibit further distal translation thereof beyond the first actuated position of trigger 62 (FIG. 4A) and the first extended position of knife 184 (FIG. 4B). A biasing member 89 disposed within housing 20 and connected between housing 20 and the free end of base 84 biases base 84 downwardly corresponding to the off-center positioning of vertical slot 88, e.g., the locked position of actuator 82.

Lock/unlock actuator 82 of knife lock assembly 80 is movable, e.g., via depression of actuator button 86 towards housing 20, against the bias of biasing member 89 from the locked position (FIGS. 3A, 4A, and 5A) to an unlocked position, wherein vertical slot 88 is centered relative to drive bar 162. In this centered position of vertical slot 88, distal mandrel 74 of slider 70 is capable of extending at least partially through vertical slot 88, sufficiently so as to permit movement of trigger 62 from the un-actuated position (FIG. 3A) or the first actuated position (FIG. 4A) to the second actuated position (FIG. 5A), thus permitting extension of knife 184 from the retracted position (FIG. 3B) or the first extended position (FIG. 4B) to the second extended position (FIG. 5B). As noted above, actuation of trigger 62 to the second actuated position (FIG. 5A) moves knife 184 to the second extended position (FIG. 5B). In this position, slider 70 is positioned such that annular slot 76 defined within distal mandrel 74 is disposed within slot 88 of base 84 of lock/unlock actuator 82. Thus, upon release of lock/unlock actuator 82, biasing member 89 urges lock/unlock actuator 82 to return to the locked position, wherein vertical slot 88 is moved to the off-center position relative to drive bar 162. With annular slot 76 of distal mandrel 74 of slider 70 disposed within slot 88 of base 84, such return of lock/unlock actuator 82 to the locked position retains slider 70 in position corresponding to the second actuated position of trigger 62 (FIG. 5A) and the second extended position of knife 184 (FIG. 5B) due to interference between distal mandrel 74 on either side of base 84 (which is received within annular slot 76 of distal mandrel 74). Accordingly, with knife 184 locked in the second extended position (FIG. 5B), knife 184 may be utilized as a scalpel, for example, to cut through tissue layers to reach tissue to be treated.

In order to release knife 184 from the second extended position (FIG. 5B), lock/unlock actuator 82 is once again depressed towards housing 20 to the unlocked position, wherein vertical slot 88 is centered relative to drive bar 162. In this centered position of vertical slot 88, similarly as detailed above, sufficient clearance is provided so as to enable distal mandrel 74 and, thus, slider 70 to return proximally relative to lock/unlock actuator 82 to the un-actuated position (FIG. 3A) or first actuated position (FIG. 4A). Once the un-actuated position (FIG. 3A) or first actuated position (FIG. 4A) has been achieved, lock/unlock actuator 82 may be released, allowing lock/unlock actuator 82 to return to its biased, locked position. With lock/unlock actuator 82 returned to the locked position, trigger 62 is once again confined to movement between the un-actuated position (FIG. 3A) and the first actuated position (FIG. 4A) and, accordingly, knife 184 is confined to movement between the retracted position (FIG. 3B) and the first extended position (FIG. 4B).

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 6:
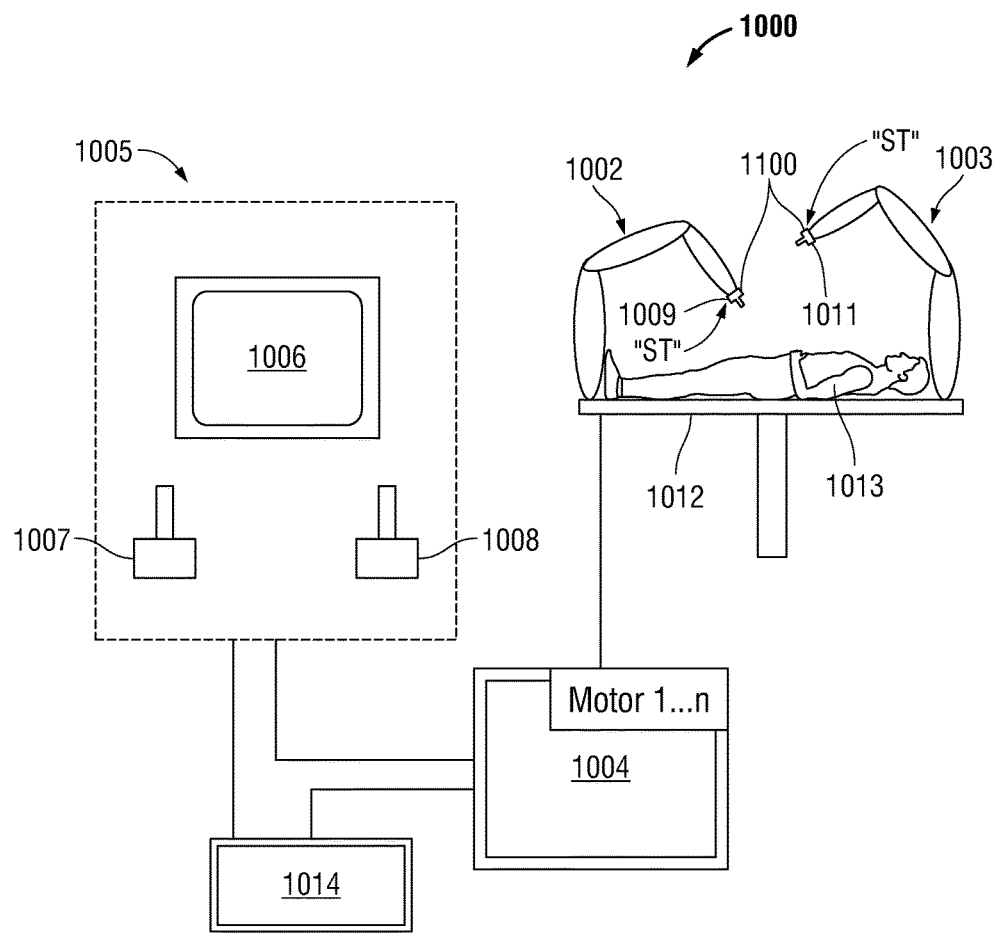
FIG. 6 is a schematic illustration of a robotic surgical system configured for use in conjunction with aspects and features of the present disclosure.

Referring to FIG. 6, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical forceps, comprising:
   a housing;
   a shaft extending distally from the housing;
   an end effector assembly disposed at a distal end of the shaft and including first and second jaw members, at least one of the first or second jaw members movable relative to the other between a spaced-apart position and an approximated position for grasping tissue therebetween;
   a movable handle extending from the housing and operably coupled to the end effector assembly, the movable handle selectively actuatable relative to the housing to move the at least one of the first or second jaw members between the spaced-apart position and the approximated position;
   a knife assembly disposed within the shaft and including a knife bar having a knife disposed at a distal end thereof, the knife bar longitudinally translatable through the shaft and relative to the end effector assembly to translate the knife between a retracted position, wherein the knife is disposed proximally of the end effector assembly, a first extended position, wherein the knife extends between the first and second jaw members, and a second extended position, wherein the knife extends distally from the first and second jaw members;
   a trigger assembly associated with the housing and including a trigger operably coupled with the knife bar such that movement of the trigger between an un-actuated position, a first actuated position, and a second actuated position moves the knife between the retracted position, the first extended position, and the second extended position, respectively, and wherein the trigger assembly includes a slider coupled between the trigger and the knife bar;
   a knife lock assembly associated with the housing, the knife lock assembly including an actuator movable independently of the movable handle between a locked position and an unlocked position, wherein, in the locked position, the trigger is movable between the un-actuated position and the first actuated position but is inhibited from moving to the second actuated position, and wherein, in the unlocked position, the trigger is movable between the un-actuated position, the first actuated position, and the second actuated position;
   wherein, with the trigger disposed in the un-actuated position or the first-actuated position and the actuator disposed in the locked position, the actuator interferes with the slider to inhibit movement of the trigger to the second actuated position,
   wherein, with the trigger disposed in the second actuated position and the actuator disposed in the locked position, the actuator engages the slider to inhibit movement of the slider, thereby retaining the trigger in the second actuated position, and,
   wherein, with the actuator disposed in the unlocked position, the actuator permits translation of the slider therethrough such that the trigger is movable between the un-actuated position or the first actuated position and the second actuated position.

2. The forceps according to claim 1, wherein the slider includes a proximal mandrel operably coupling the trigger with the knife bar and a distal mandrel operably associated with the actuator.

3. The forceps according to claim 1, wherein the actuator is biased towards the locked position.

4. The forceps according to claim 1, wherein the actuator includes an actuator button disposed on the housing, the actuator button selectively depressible relative to the housing to move the actuator from the locked position to the unlocked position.

5. The forceps according to claim 1, further including:
   a drive assembly including a drive bar slidably disposed within the shaft, the drive bar coupled to at least one of the first or second jaw members at a distal end thereof,
   wherein the drive bar is operably coupled between the movable handle and the at least one of the first or second jaw members such that movement of the movable handle moves the at least one of the first or second jaw members between the spaced-apart position and the approximated position.

6. The forceps according to claim 1, wherein each of the first and second jaw members includes an electrically-conductive surface adapted to connect to a source of energy for treating the tissue grasped between the first and second jaw members.

7. The forceps according to claim 1, wherein each of the first and second jaw members defines a knife slot configured to permit reciprocation of the knife therethrough.

* * * * *